United States Patent
Semler et al.

(10) Patent No.: US 12,295,858 B2
(45) Date of Patent: May 13, 2025

(54) EXPANDABLE VERTEBRAL BODY REPLACEMENT DEVICE AND METHOD

(71) Applicant: MUSC FOUNDATION FOR RESEARCH DEVELOPMENT, Charleston, SC (US)

(72) Inventors: Mark Evald Semler, Mount Pleasant, SC (US); Bruce Frankel, Mount Pleasant, SC (US); Joseph Ruscito, Charleston, SC (US)

(73) Assignee: MUSC FOUNDATION FOR RESEARCH DEVELOPMENT, Charleston, SC (US)

(*) Notice: Subject to any disclaimer, the term of this patent is extended or adjusted under 35 U.S.C. 154(b) by 332 days.

(21) Appl. No.: 17/821,995

(22) Filed: Aug. 24, 2022

(65) Prior Publication Data
US 2022/0401227 A1    Dec. 22, 2022

Related U.S. Application Data

(63) Continuation of application No. PCT/US2021/070183, filed on Feb. 24, 2021.

(60) Provisional application No. 62/980,824, filed on Feb. 24, 2020.

(51) Int. Cl.
*A61F 2/44* (2006.01)
*A61F 2/30* (2006.01)

(52) U.S. Cl.
CPC .. *A61F 2/4455* (2013.01); *A61F 2002/30364* (2013.01); *A61F 2002/30383* (2013.01)

(58) Field of Classification Search
CPC ...... A61F 2/442; A61F 2/4425; A61F 2/4455; A61F 2002/443

USPC .......................................... 623/17.11–17.16
See application file for complete search history.

(56) References Cited

U.S. PATENT DOCUMENTS

| | | | |
|---|---|---|---|
| 4,401,112 A | 8/1983 | Rezaian |
| 4,553,273 A | 11/1985 | Wu |
| 4,657,550 A | 4/1987 | Daher |
| 5,083,621 A | 1/1992 | Sheridan |
| 5,336,223 A | 8/1994 | Rogers |

(Continued)

FOREIGN PATENT DOCUMENTS

| | | |
|---|---|---|
| WO | 20100124008 | 10/2010 |
| WO | 20130003736 | 1/2013 |

(Continued)

OTHER PUBLICATIONS

International Search Report and Written Opinion of the International Searching Authority for PCT/US2021/070183, Apr. 29, 2021, 10 pages.

*Primary Examiner* — Ellen C Hammond
*Assistant Examiner* — Christina NegrelliRodriguez
(74) *Attorney, Agent, or Firm* — Heslin Rothenberg Farley & Mesiti P.C.; Jacquelyn A. Graff, Esq.

(57) ABSTRACT

An expandable vertebral body implant, and methods of assembly and using the implant. The vertebral body implant includes a body with a first end and a second end, a rotating member rotatably coupled to the first end of the body, wherein an end includes a plurality of first notches inset into the rotating member, an extension member moveably coupled to the rotating member, and a locking member positioned on an interior of the body. Methods for assembling and using the vertebral body implant are also disclosed.

18 Claims, 13 Drawing Sheets

(56) References Cited

U.S. PATENT DOCUMENTS

| | | |
|---|---|---|
| 5,571,192 A | 11/1996 | Schonhoffer |
| 5,702,453 A | 12/1997 | Rabbe |
| 5,702,455 A | 12/1997 | Saggar |
| 5,776,198 A | 7/1998 | Rabbe |
| 5,989,290 A | 11/1999 | Biedermann |
| 6,176,881 B1 | 1/2001 | Schar |
| 6,190,413 B1 | 2/2001 | Sutcliffe |
| 6,344,057 B1 | 2/2002 | Rabbe |
| 6,524,341 B2 | 2/2003 | Lang |
| 6,730,088 B2 | 5/2004 | Yeh |
| 6,752,832 B2 | 6/2004 | Neumann |
| 6,802,867 B2 | 10/2004 | Manasas |
| 6,902,579 B2 | 6/2005 | Harms |
| 7,056,343 B2 | 6/2006 | Schafer |
| 7,384,431 B2 | 6/2008 | Berry |
| 7,547,325 B2 | 6/2009 | Biedermann |
| 7,575,601 B2 | 8/2009 | Dickson |
| 7,588,573 B2 | 9/2009 | Berry |
| 7,608,078 B2 | 10/2009 | Berry |
| 7,641,693 B2 | 1/2010 | Gutlin |
| 7,674,296 B2 | 3/2010 | Rhoda |
| 7,758,648 B2 | 7/2010 | Castleman |
| 7,811,327 B2 | 10/2010 | Hansell |
| 7,879,096 B2 | 2/2011 | Dickson |
| 7,909,870 B2 | 3/2011 | Kraus |
| 7,914,581 B2 | 3/2011 | Dickson |
| 7,981,157 B2 | 7/2011 | Castleman |
| 8,142,441 B2 | 3/2012 | Refai |
| 8,157,864 B2 | 4/2012 | Rogeau |
| 8,182,535 B2 | 5/2012 | Kraus |
| 8,182,537 B2 | 5/2012 | Refai |
| 8,197,546 B2 | 6/2012 | Doubler |
| 8,231,681 B2 | 7/2012 | Castleman |
| 8,241,363 B2 | 8/2012 | Sommerich |
| 8,246,680 B2 | 8/2012 | Betz |
| 8,252,054 B2 | 8/2012 | Greenhalgh |
| 8,267,998 B2 | 9/2012 | Kraus |
| 8,268,004 B2 | 9/2012 | Castleman |
| 8,282,683 B2 | 10/2012 | Mclaughlin |
| 8,292,963 B2 | 10/2012 | Miller |
| 8,308,802 B2 | 11/2012 | Rhoda |
| 8,337,559 B2 | 12/2012 | Hansell |
| 8,366,779 B2 | 2/2013 | Dickson |
| 8,377,140 B2 | 2/2013 | DeFalco |
| 8,540,770 B2 | 9/2013 | Woodburn, Sr. |
| 8,568,482 B2 | 10/2013 | Kraus |
| 8,585,763 B2 | 11/2013 | Olevsky |
| 8,591,585 B2 | 11/2013 | McLaughlin |
| 8,591,587 B2 * | 11/2013 | Refai ............ A61F 2/4637 623/17.15 |
| 8,603,173 B2 | 12/2013 | Biedermann |
| 8,668,740 B2 | 3/2014 | Rhoda |
| 8,690,886 B2 | 4/2014 | Fedorov |
| 8,690,950 B2 | 4/2014 | Refai |
| 8,702,719 B2 | 4/2014 | Refai |
| 8,721,723 B2 | 5/2014 | Hansell |
| 8,740,980 B2 | 6/2014 | Merves |
| 8,801,788 B2 | 8/2014 | Merves |
| 8,870,880 B2 | 10/2014 | Himmelberger |
| 8,992,617 B2 * | 3/2015 | Woodburn ............ A61F 2/44 623/17.15 |
| 9,023,108 B2 | 5/2015 | Hansell |
| 9,034,046 B2 | 5/2015 | Refai |
| 9,050,195 B2 | 6/2015 | DeFalco |
| 9,138,324 B2 | 9/2015 | Prevost |
| 9,144,503 B2 | 9/2015 | Stinchfield |
| 9,173,747 B2 | 11/2015 | Hansell |
| 9,180,018 B2 | 11/2015 | Hansell |
| 9,192,481 B2 | 11/2015 | Rhoda |
| 9,211,193 B2 | 12/2015 | Aubert |
| 9,241,808 B2 | 1/2016 | Sabatino |
| 9,271,842 B2 | 3/2016 | Davenport |
| 9,301,850 B2 | 4/2016 | McLaughlin |
| 9,320,612 B2 | 4/2016 | Sournac |
| 9,345,588 B2 | 5/2016 | Himmelberger |
| 9,387,090 B2 | 7/2016 | Arnold |
| 9,393,128 B2 | 7/2016 | Hansell |
| 9,474,621 B2 | 10/2016 | McLaughlin |
| 9,572,678 B2 | 2/2017 | Nichols |
| 9,579,211 B2 | 2/2017 | McLaughlin |
| 9,636,231 B2 | 5/2017 | Rhoda |
| 9,636,233 B2 | 5/2017 | Arnold |
| 9,655,738 B2 | 5/2017 | Stinchfield |
| 9,681,961 B2 | 6/2017 | Prevost |
| 9,687,357 B2 | 6/2017 | Bannigan |
| 9,707,091 B2 | 7/2017 | McLaughlin |
| 9,707,096 B2 | 7/2017 | Sutterlin, III |
| 2004/0059271 A1 | 3/2004 | Berry |
| 2004/0172129 A1 | 9/2004 | Schafer |
| 2004/0186569 A1 | 9/2004 | Berry |
| 2005/0187634 A1 | 8/2005 | Berry |
| 2006/0074490 A1 | 4/2006 | Sweeney |
| 2007/0028710 A1 | 2/2007 | Kraus |
| 2007/0255407 A1 | 11/2007 | Castleman |
| 2007/0255421 A1 | 11/2007 | Dickson |
| 2008/0167720 A1 | 7/2008 | Melkent |
| 2009/0112325 A1 | 4/2009 | Refai |
| 2010/0016971 A1 | 1/2010 | Berry |
| 2010/0094424 A1 | 4/2010 | Woodburn |
| 2010/0211119 A1 | 8/2010 | Refai |
| 2010/0274357 A1 | 10/2010 | Miller |
| 2011/0087328 A1 | 4/2011 | Dickson |
| 2011/0184524 A1 | 7/2011 | Wiedenbeck |
| 2012/0197403 A1 | 8/2012 | Merves |
| 2012/0209384 A1 * | 8/2012 | Arnold ............ A61F 2/28 623/17.15 |
| 2012/0265303 A1 | 10/2012 | Refai |
| 2012/0330426 A1 | 12/2012 | McLaughlin |
| 2013/0053965 A1 | 2/2013 | Metz-Stavenhagen |
| 2013/0310938 A1 | 11/2013 | Sournac |
| 2013/0331943 A1 | 12/2013 | Arnold et al. |
| 2014/0052249 A1 | 2/2014 | Metz-Stavenhagen |
| 2014/0058517 A1 | 2/2014 | Sabatino |
| 2014/0088708 A1 | 3/2014 | McLaughlin |
| 2014/0107786 A1 | 4/2014 | Geisler et al. |
| 2014/0156006 A1 | 6/2014 | Bannigan et al. |
| 2014/0222151 A1 | 8/2014 | Refai et al. |
| 2015/0018953 A1 * | 1/2015 | Frasier ............ A61F 2/4465 623/17.15 |
| 2016/0022435 A1 | 1/2016 | Hansell et al. |
| 2016/0022436 A1 | 1/2016 | Hansell et al. |
| 2016/0045327 A1 * | 2/2016 | Robinson ............ A61F 2/447 623/17.15 |
| 2016/0051370 A9 | 2/2016 | Hansell et al. |
| 2016/0199192 A1 | 7/2016 | McLaughlin et al. |
| 2016/0235553 A1 | 8/2016 | Himmelberger et al. |
| 2016/0278933 A1 | 9/2016 | Semler et al. |
| 2017/0007423 A1 | 1/2017 | McLaughlin et al. |
| 2017/0143510 A1 | 5/2017 | Nichols et al. |
| 2017/0216050 A1 | 8/2017 | Semler et al. |
| 2017/0224507 A1 | 8/2017 | Arnold et al. |
| 2018/0014942 A1 | 1/2018 | Semler et al. |

FOREIGN PATENT DOCUMENTS

| | | |
|---|---|---|
| WO | 20130003738 | 1/2013 |
| WO | 20130173682 | 11/2013 |
| WO | 20160153742 | 9/2016 |
| WO | 2018097857 | 5/2018 |

* cited by examiner

EXPANDABLE VERTEBRAL BODY REPLACEMENT DEVICE AND METHOD

CROSS REFERENCE TO RELATED APPLICATION

This application is a continuation of PCT Application No. PCT/US2021/070183 filed Feb. 24, 2021, and entitled "Expandable Vertebral Body Replacement Device and Method," which claims priority benefit under 35 U.S.C. § 119(e) of U.S. provisional application No. 62/980,824 filed Feb. 24, 2020, which are incorporated herein by reference in their entireties. This application also relates to U.S. application Ser. No. 16/424,455 filed May 28, 2019 which is a continuation-in-part of International Application No. PCT/US2017/031093 filed May 4, 2017 and published as WO 2018/097857 on May 31, 2018, which claims priority benefit under 35 U.S.C. § 119(e) of U.S. provisional patent application No. 62/427,149 filed Nov. 28, 2016, which are incorporated herein by reference in their entireties. In addition, this application is related to International Application No. PCT/US2016/020209 filed Mar. 1, 2016 and published as WO 2016/153742 on Sep. 26, 2016, which claims priority to U.S. application Ser. No. 14/665,833 filed Mar. 23, 2015 and issued as U.S. Pat. No. 9,775,719 on Oct. 3, 2017, which are incorporated herein by reference in their entireties. Further, this application relates to U.S. application Ser. No. 15/486,739 filed on Apr. 13, 2017 and issued as U.S. Pat. No. 9,889,018 on Feb. 13, 2018, which claims priority to U.S. Application No. 62/427,149 filed Nov. 28, 2016 and which is a continuation-in-part of U.S. application Ser. No. 14/665,833 filed Mar. 23, 2015 and issued as U.S. Pat. No. 9,775,719 on Oct. 3, 2017, which are incorporated herein by reference in their entireties. Finally, this application relates to U.S. application Ser. No. 15/719,192 filed Sep. 28, 2017, which is a continuation of U.S. application Ser. No. 14/665,833 filed Mar. 23, 2015 and issued as U.S. Pat. No. 9,775,719 on Oct. 3, 2017, which are incorporated herein by reference in their entireties.

FIELD OF THE INVENTION

The present disclosure relates generally to medical implants for insertion in a space between a patient's vertebrae. More specifically, but not exclusively, the present disclosure concerns expandable vertebral body replacement devices for implantation in a patient's spine between the vertebrae.

BACKGROUND OF THE INVENTION

Trauma or disease, such as, tumors may cause pressure on a patient's spinal cord. In order to alleviate the pressure and likely the pain it is causing, surgeons may remove part or all of a patient's vertebral bodies and adjacent vertebral discs in the location of the pressure, during a procedure, such as, a corpectomy. Often implants are used to replace the removed vertebral bodies to maintain the space between the remaining vertebral bodies.

SUMMARY OF THE INVENTION

Aspects of the present disclosure provide expanding vertebral body replacement devices for implantation in a patient's spine between the vertebrae and methods of using the same.

In one aspect, provided herein is a vertebral body implant, including a body with a first end and a second end, a rotating member rotatably coupled to the first end of the body, wherein an end includes a plurality of first notches inset into the rotating member, an extension member moveably coupled to the rotating member, and a locking member positioned on an interior of the body.

In another aspect, provided herein is a method for assembling the vertebral body implant, including obtaining a body with a rotating member rotatably coupled to the body. The method also includes inserting a locking member into a through hole of the body and positioning the locking member on an interior surface of the body. The method further includes inserting an extension member into a first end of the rotating member and a first end of the body and rotating the rotating member to translate the extension member to an undeployed position. In addition, the method includes coupling a first end plate to a first end of the extension member with a first retaining member and coupling a second end plate to a second end of the body with a second retaining member.

In yet another aspect, provided herein is a method for using a vertebral body implant, including obtaining the vertebral body implant. The vertebral body implant including a body with a first end and a second end, a rotating member rotatably coupled to the first end of the body, wherein an end includes a plurality of first notches inset into the rotating member, an extension member moveably coupled to the rotating member, and a locking member positioned on an interior of the body. The method also includes obtaining an insertion instrument and coupling the vertebral body implant to the insertion instrument. In addition, the method includes inserting the vertebral body implant into a patient between two vertebral bodies and engaging the plurality of first notches in the rotating member to translate the extension member in a first direction to expand the vertebral body implant. Finally, the method includes removing the insertion instrument.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Generally stated, disclosed herein is an expandable vertebral body replacement device. Further, methods of assembling and using the expandable vertebral body replacement device are discussed.

In this detailed description and the following claims, the words proximal, distal, anterior, posterior, medial, lateral, superior, inferior, cephalad, and caudal are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above, "inferior" means a direction below another object or structure, "cephalad" means a direction toward the head, and "caudal" means a direction toward the inferior part of the body.

Figure 1:
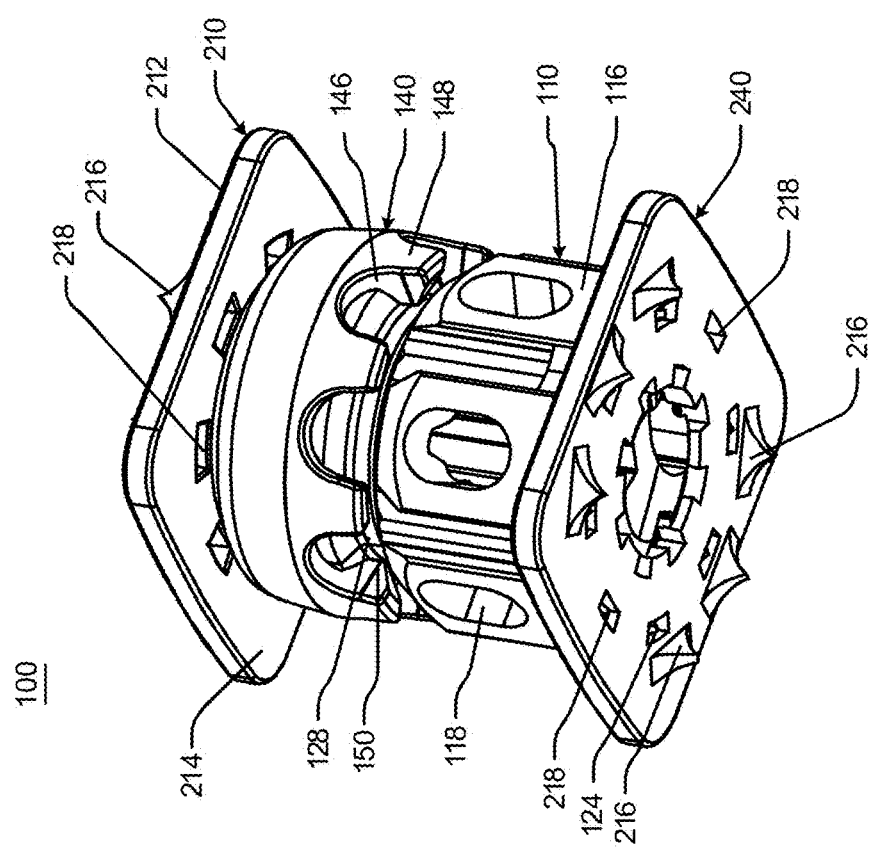
FIG. 1 is a first end, perspective view of an embodiment of a vertebral body implant in a retracted position, in accordance with an aspect of the present disclosure.
Figure 2:
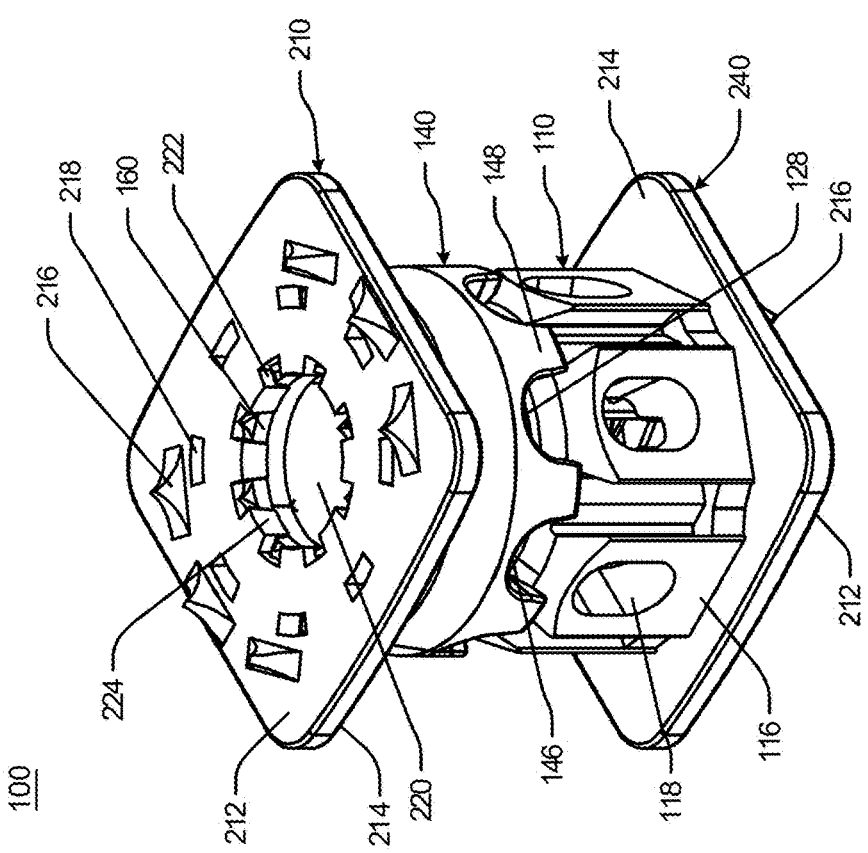
FIG. 2 is a second end, perspective view of the implant of FIG. 1, in accordance with an aspect of the present disclosure.
Figure 4:
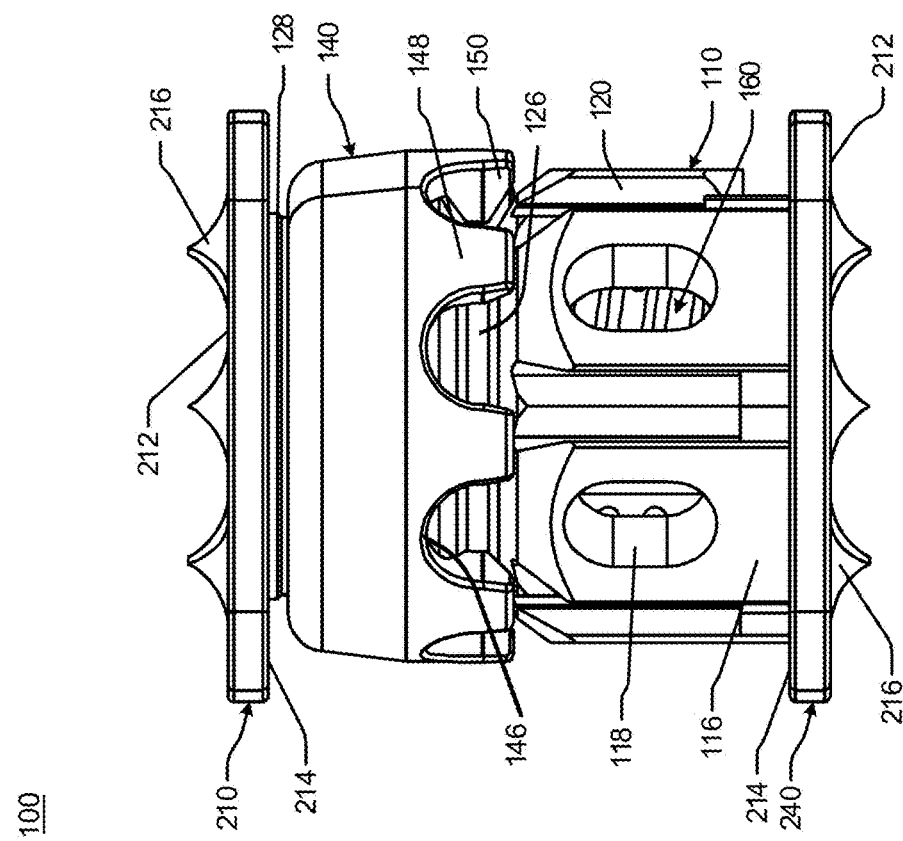
FIG. 4 is a second side view of the implant of FIG. 1, in accordance with an aspect of the present disclosure.
Figure 3:
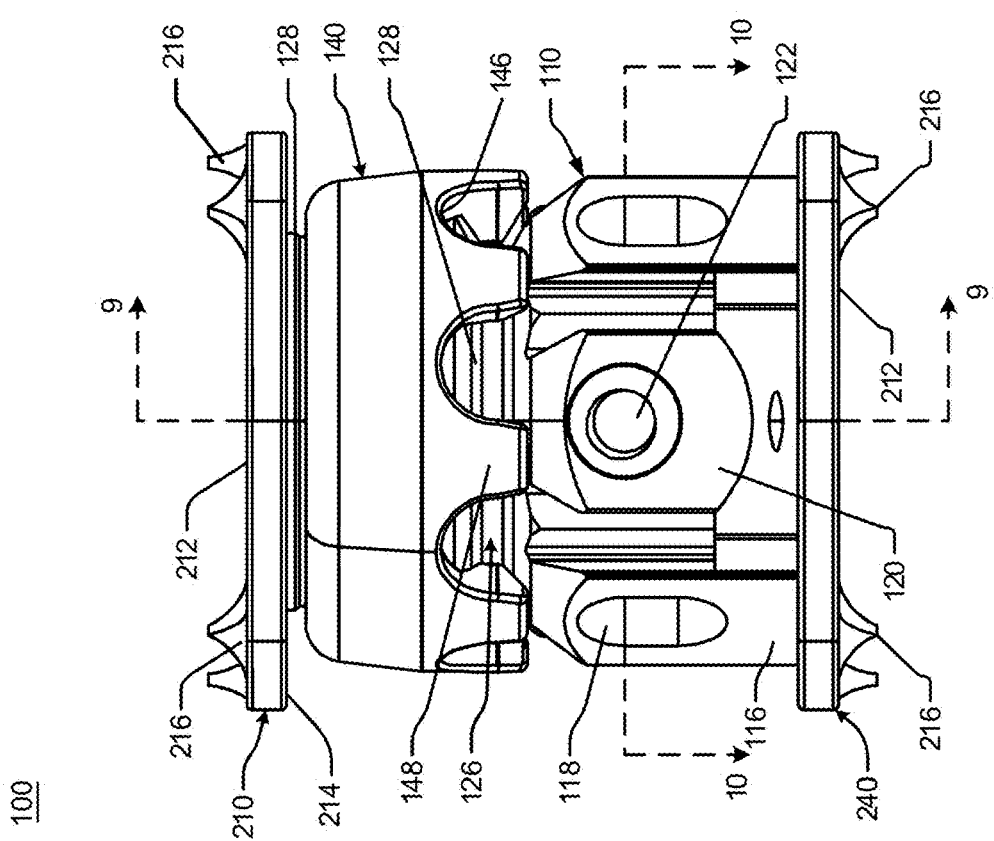
FIG. 3 is a first side view of the implant of FIG. 1, in accordance with an aspect of the present disclosure.
Figure 6:
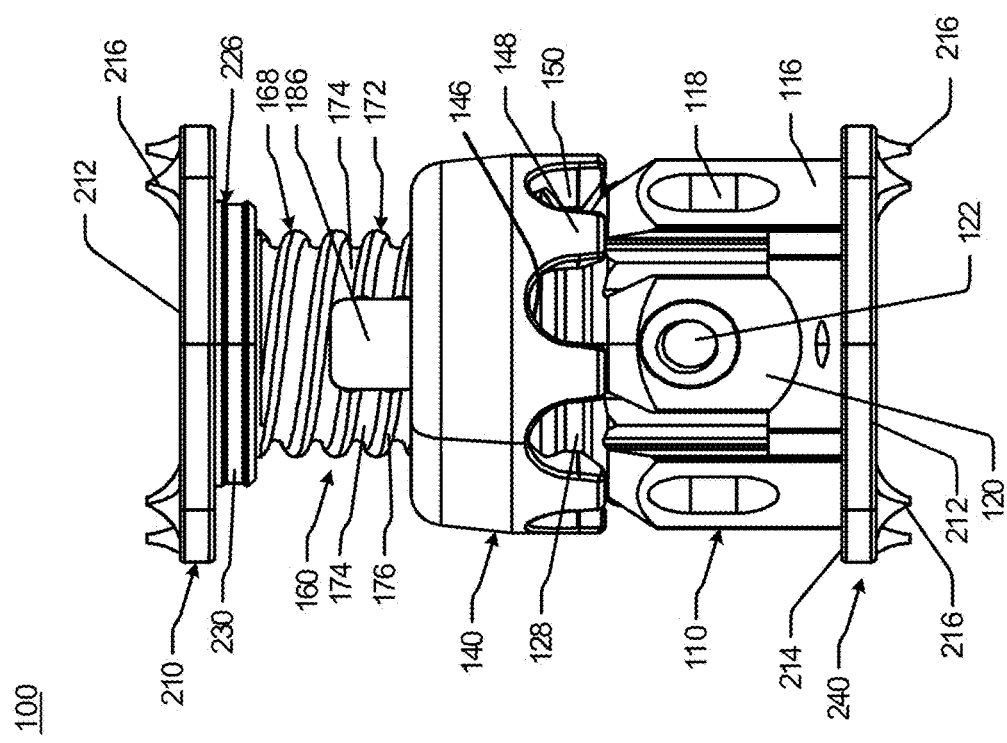
FIG. 6 is a first side view of the implant of FIG. 5, in accordance with an aspect of the present disclosure.
Figure 5:
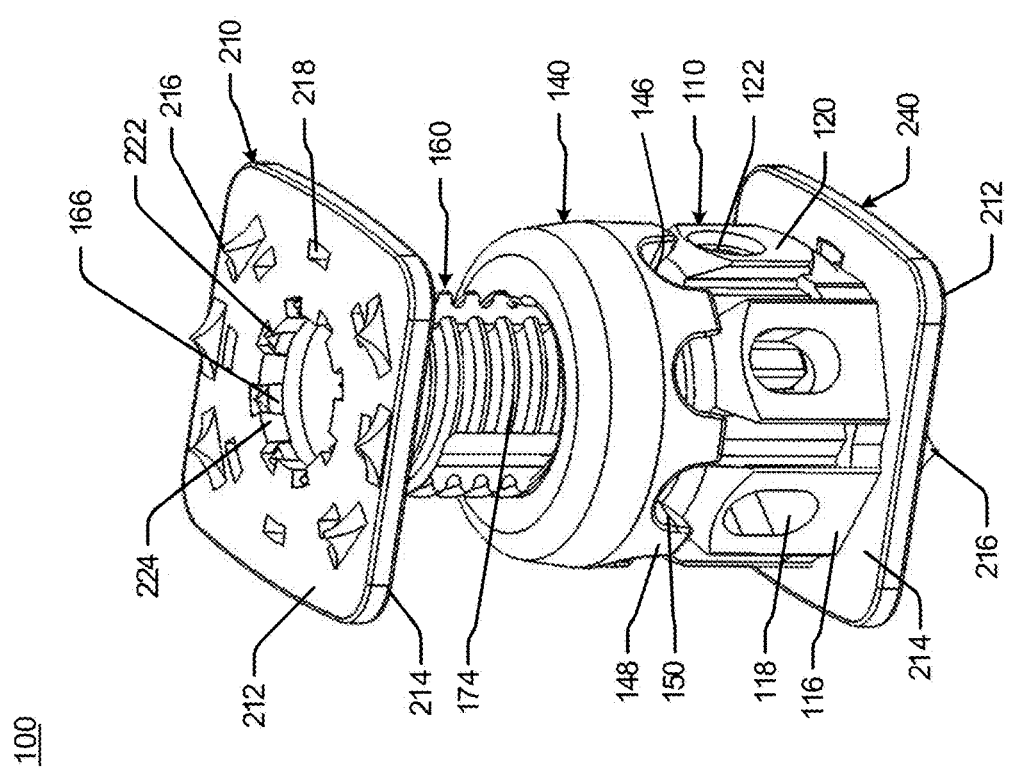
FIG. 5 is a first end, perspective view of the implant of FIG. 1 in a deployed position, in accordance with an aspect of the present disclosure.
Figure 8:
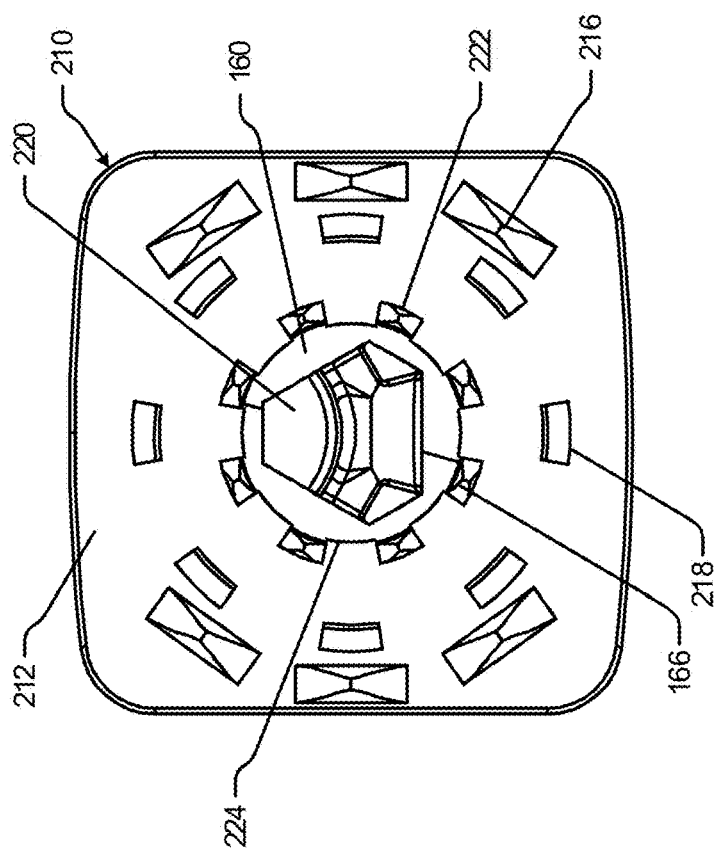
FIG. 8 is a first end view of the implant of FIG. 5, in accordance with an aspect of the present disclosure.
Figure 7:
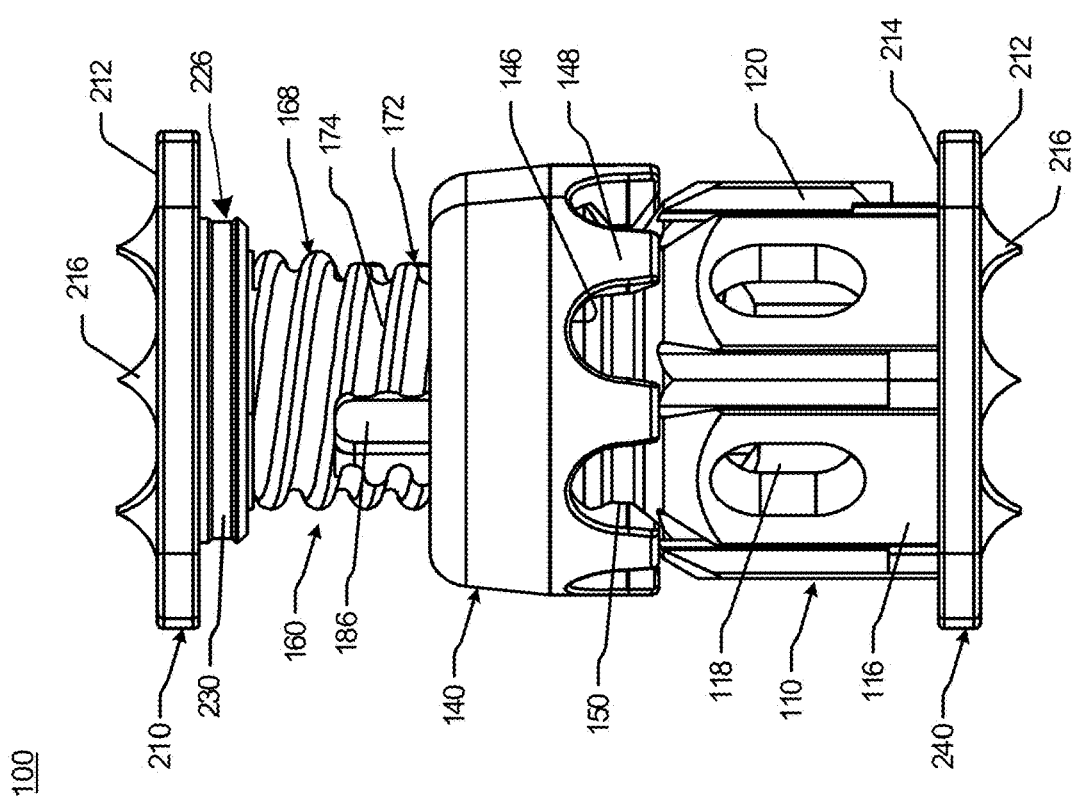
FIG. 7 is a second side view of the implant of FIG. 5, in accordance with an aspect of the present disclosure.
Figure 10:
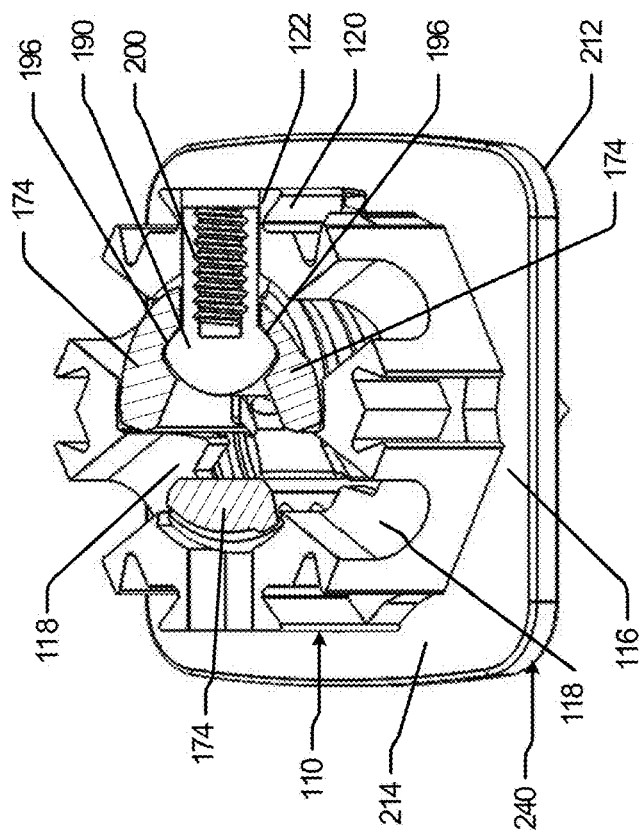
FIG. 10 is a cross-sectional view of the implant of FIG. 1 taken along line 10-10 in FIG. 3, in accordance with an aspect of the present disclosure.
Figure 9:
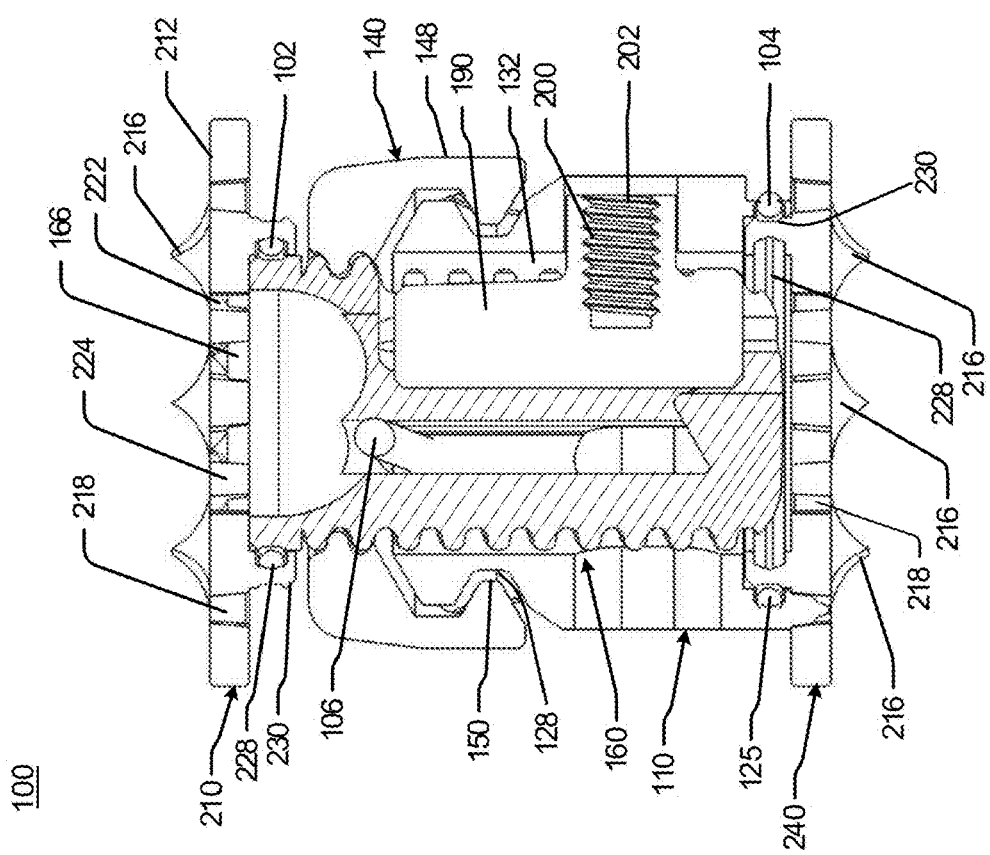
FIG. 9 is a cross-sectional view of the implant of FIG. 1 taken along line 9-9 in FIG. 3, in accordance with an aspect of the present disclosure.
Figure 12:
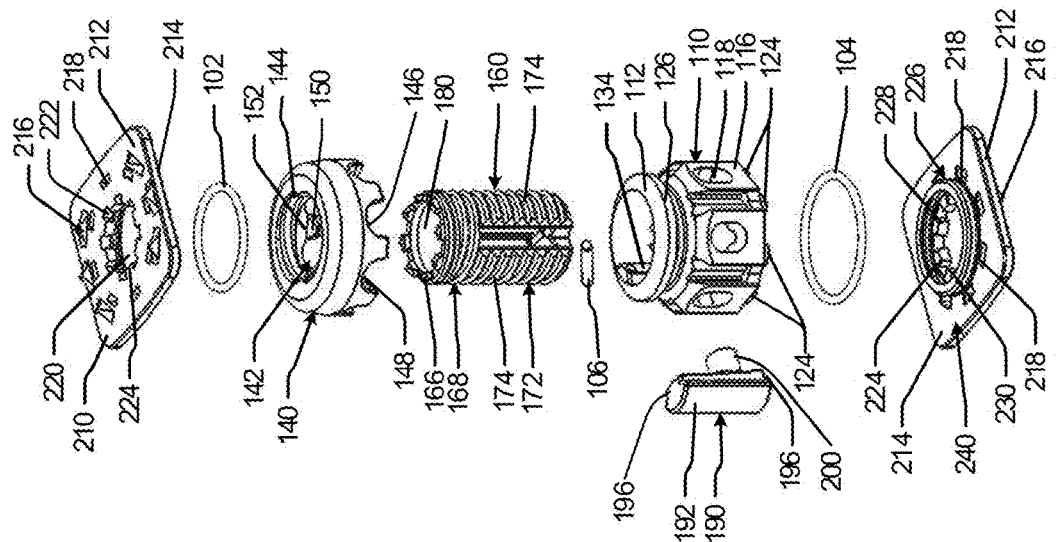
FIG. 12 is an exploded, first end perspective view of the implant of FIG. 1, in accordance with an aspect of the present disclosure.
Figure 11:
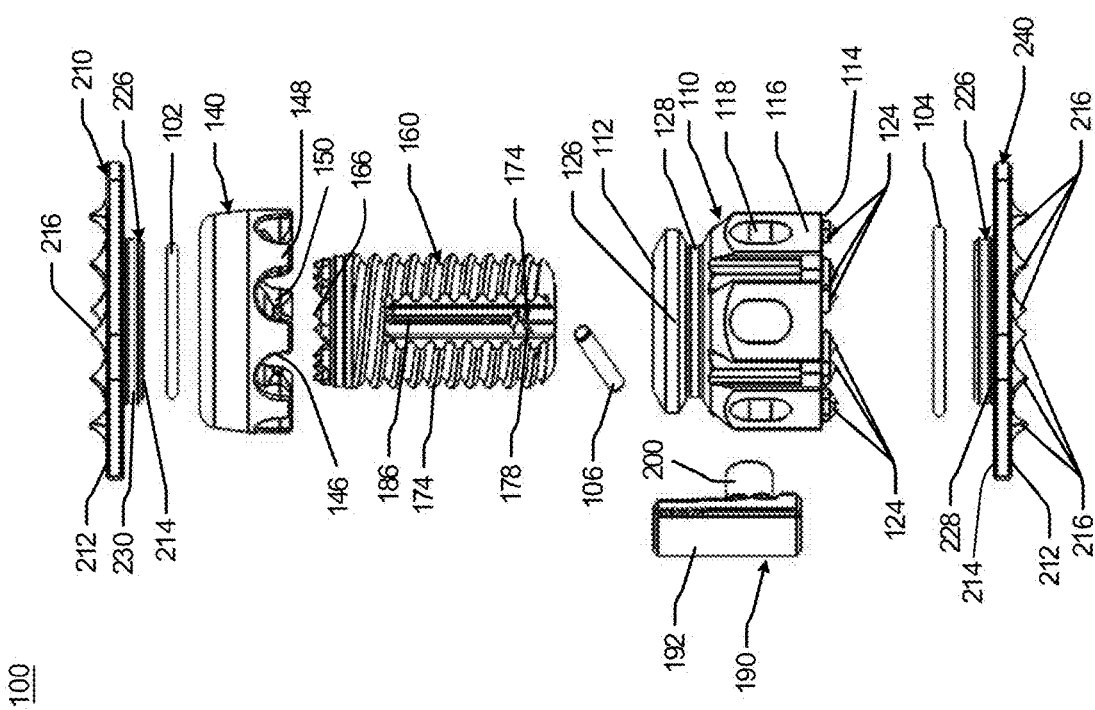
FIG. 11 is an exploded, side view of the implant of FIG. 1, in accordance with an aspect of the present disclosure.

Referring to the drawings, wherein like reference numerals are used to indicate like or analogous components throughout the several views, and with particular reference to FIGS. 1-28, there is illustrated an exemplary embodiment of a vertebral body replacement implant 100. The vertebral body implant 100 may include a body 110, a rotating member 140 rotatably coupled to the first end 112 of the body 110, an extension member 160 moveably inserted through the first end 112 of the body 110, and a locking or securement member 190 coupled to an interior surface 132 of the body 110. The vertebral body implant 100 may also include at least one end plate 210, 240, 250 coupled to at least one end of the implant 100. As shown in at least FIGS. 1-9, a first end plate 210 may be coupled to a first end 162 of the extension member 160 and a second end plate 240 may be coupled to a second end 114 of the body 110. The first end plate 210 may be secured to the extension member 160 by a first retaining member or O-ring 102, as shown in FIGS. 9, 11 and 12, and the second end plate 240 may be secured to the body 110 by a second retaining member or O-ring 104, as shown in FIGS. 9, 11 and 12. The implant 100 may also include a pin 106 for insertion through the body 110 and a through hole 186 of the extension member 160 for engagement with a support member or stop pin seat 178 of the extension member 160.

With continued reference to FIGS. 1-12 and 19-22, the body 110 includes a first end 112 and a second end 114 positioned opposite the first end 112. The body 110 may also include a plurality of side members 116 positioned around the circumference of the body 110. The side members 116 may be, for example, planar surfaces extending between at least a portion of the first end 112 and the second end 114. The side members 116 may also include, for example, beveled or angled sides extending between the planar surfaces and the body 110, as shown in at least FIG. 10. The side members 116 may each include, for example, an opening 118 extending through the side members 116 from an exterior surface of the body 110 to an interior surface. The openings 118 may be, for example, oblong openings with the longitudinal axis of the openings 118 being positioned parallel to the longitudinal axis of the body 110. In addition, at least one side surface 116 may include a locking portion or locking protrusion 120 extending out from the exterior surface of the body 110. The locking portion 120 may also include an opening 122 extending through the locking portion 120 from an exterior surface to an interior surface of the body 110. The opening 122, may be, for example, round or circular to receive a corresponding portion of the locking member or securement member 190.

Figure 20:
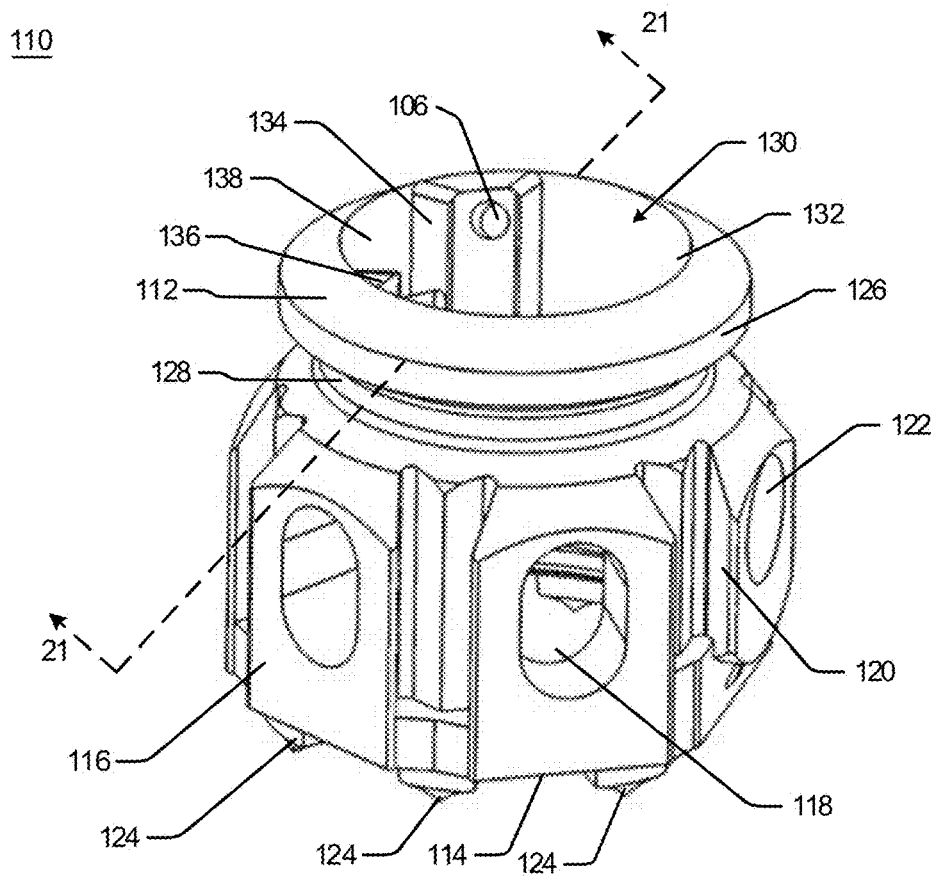
FIG. 20 is a first end perspective view of the body of FIG. 19, in accordance with an aspect of the present disclosure.
Figure 21:
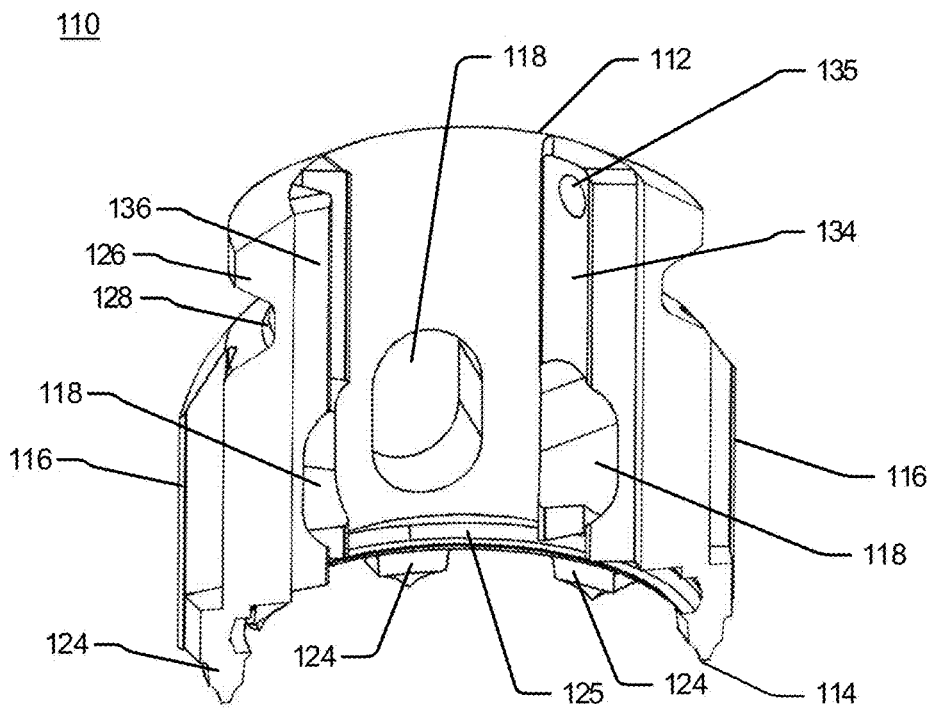
FIG. 21 is a cross-sectional view of the body of FIG. 19 taken along line 21-21 in FIG. 20, in accordance with an aspect of the present disclosure.

As shown in FIGS. 11, 12 and 19-21, the body 110 may also include a plurality of pegs or engagement members 124 extending away from the second end 114. The engagement members 124 may have, for example, a polygonal shape with a generally rectangular cross-sectional shape and a pointed or triangularly shaped tip. The second end 114 may also include an interior slot 125 extending into an interior surface 132 of the body 110, as shown in FIGS. 9 and 21. The interior slot 125 may be, for example, sized and shaped or configured to receive an O-ring 104 to secure an end plate 240 to the second end 114 of the body 110. The body 110 may further include a rim or circumferential protrusion 126 positioned at the first end 112, as shown in at least FIGS. 11, 12, 19 and 20. A groove 128 may be inset into the exterior surface of the body 110 inferior to the rim 126 forming a recessed region below the rim 126. The rim 126 and groove 128 may be, for example, configured or sized and shaped to engage the interior surface of a rotating member 140, as described in greater detail below.

Figure 22:
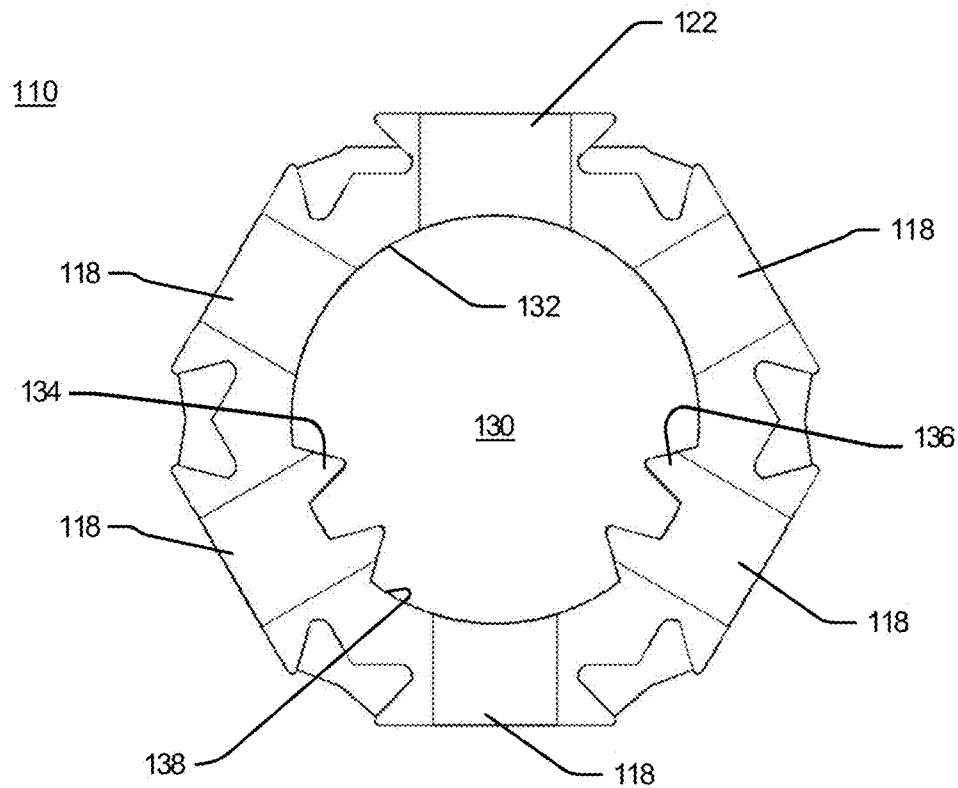
FIG. 22 is a cross-sectional view of the body of FIG. 19 taken along line 22-22 in FIG. 19, in accordance with an aspect of the present disclosure.

The body 110 may also include a through hole 130 extending through the interior of the body 110 from the first end 112 to the second end 114, as shown in at least FIGS. 9, 10, 12, 20 and 21. The through hole 130 may form an interior surface 132 within the body 110. The body 110 may also include a first alignment protrusion 134 and a second alignment protrusion 136 each extending from the interior surface 132 into the hole 130. The first alignment protrusion 134 may have, for example, a curved interior surface and angled sides extending from the interior surface of the protrusion 134 to the interior surface 132 of the body 110. The first alignment protrusion 134 may extend from the first end 112 to the interior slot 125 at the second end 116 of the body 110. The opening 118 may also extend through the first alignment protrusion 134, such that, the opening 118 extends through at least one side member 116 of the body 110 and the first alignment protrusion 134 perpendicular to a longitudinal axis of the protrusion 134, as shown in FIG. 21. The first alignment protrusion 134 may also include a locking hole 135 positioned, for example, near the first end 112 of the body 110, as also shown in FIG. 21. The locking hole 135 may be, for example, sized and shaped or configured to receive the pin 106. The second alignment protrusion 136 may be, for example, spaced radially from the first alignment protrusion 134, as shown in FIG. 22. The second alignment protrusion 136 may include, for example, two generally triangularly shaped protrusions spaced apart from each other and angled in towards one another. The second alignment protrusion 136 may extend between the first end 112 and the interior slot 125 at the second end 116 of the body 110. The second alignment protrusion 136 may also include an opening 118 extending through the body 110 and the second alignment protrusion 136 perpendicular to a longitudinal axis of the protrusion 136, as shown in FIG. 21. A channel 138 is positioned between or formed by the first alignment protrusion 134 and the second alignment protrusion 136, as shown in FIGS. 20-22.

Referring now to FIGS. 1-7, 9, 11, and 12, the rotating member 140 is shown. The rotating member 140 may include a center opening 142 extending through the rotating member 140. The exterior surface of the rotating member 140 may include a plurality of grooves, notches, gear teeth, or scallops 146, as best seen in FIGS. 11 and 12. The plurality of notches 146 may be, for example, sized and shaped or configured to receive an insertion tool (not shown). The rotating member 140 may also include threads 144 on the interior surface of the member 140, as shown in FIGS. 9 and 12. In addition, the rotating member 140 may include at least one protrusion 150 positioned between each notch 146 to engage the groove 128 in the body 110. The rotating member 140 may also include a recess, cavity or undercut 152 positioned superior to the at least one protrusion 150 on the interior surface of the rotating member 140. The recess 152 may be, for example, sized and shaped or configured to receive the circumferential rim 126 of the body 110, as shown in FIG. 9.

Figure 24:
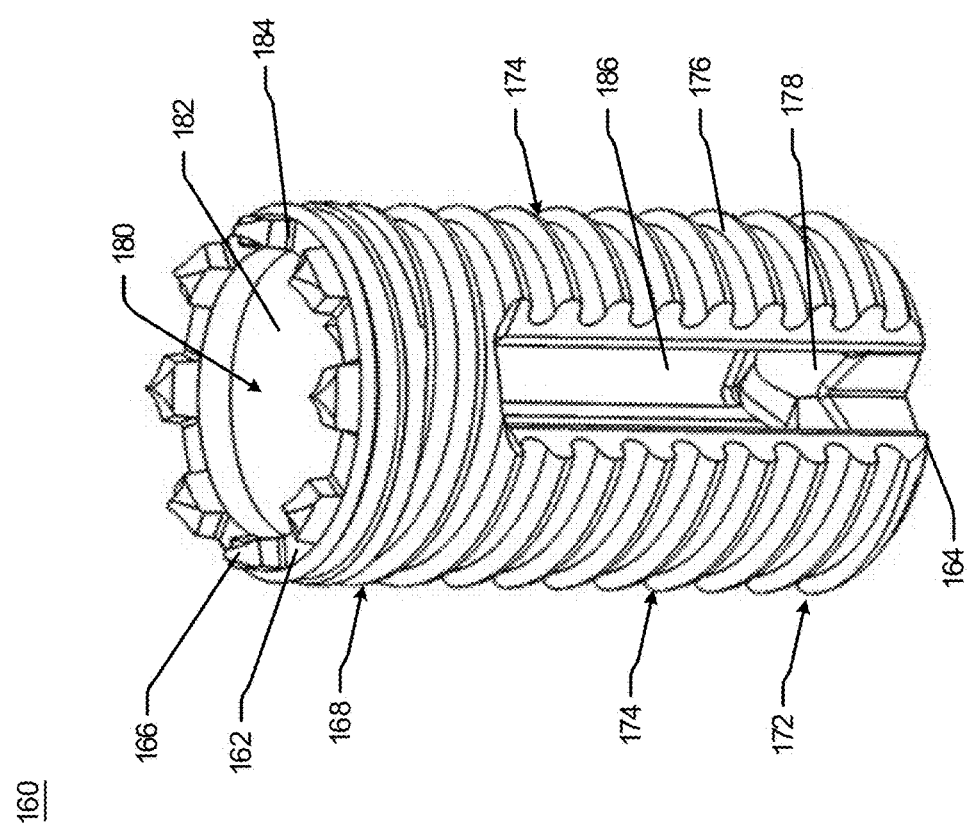
FIG. 24 is a perspective view of the extension member of FIG. 21, in accordance with an aspect of the present disclosure.
Figure 23:
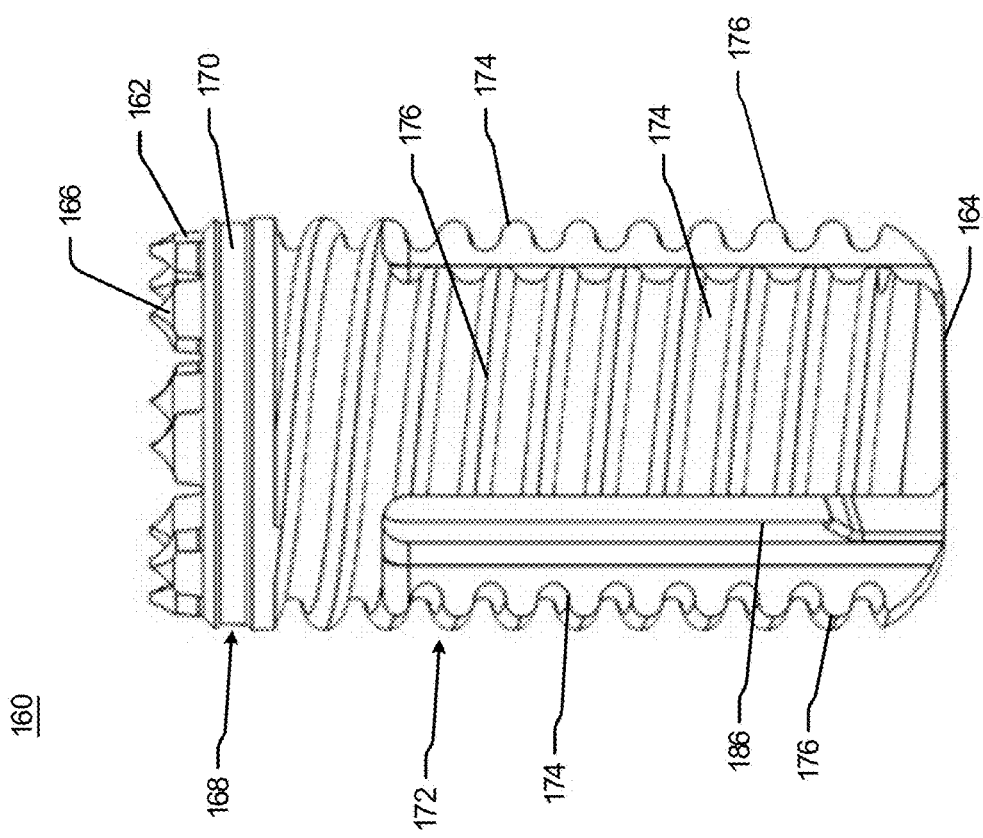
FIG. 23 is a side view of an extension member of the implant of FIG. 1, in accordance with an aspect of the present disclosure.
Figure 25:
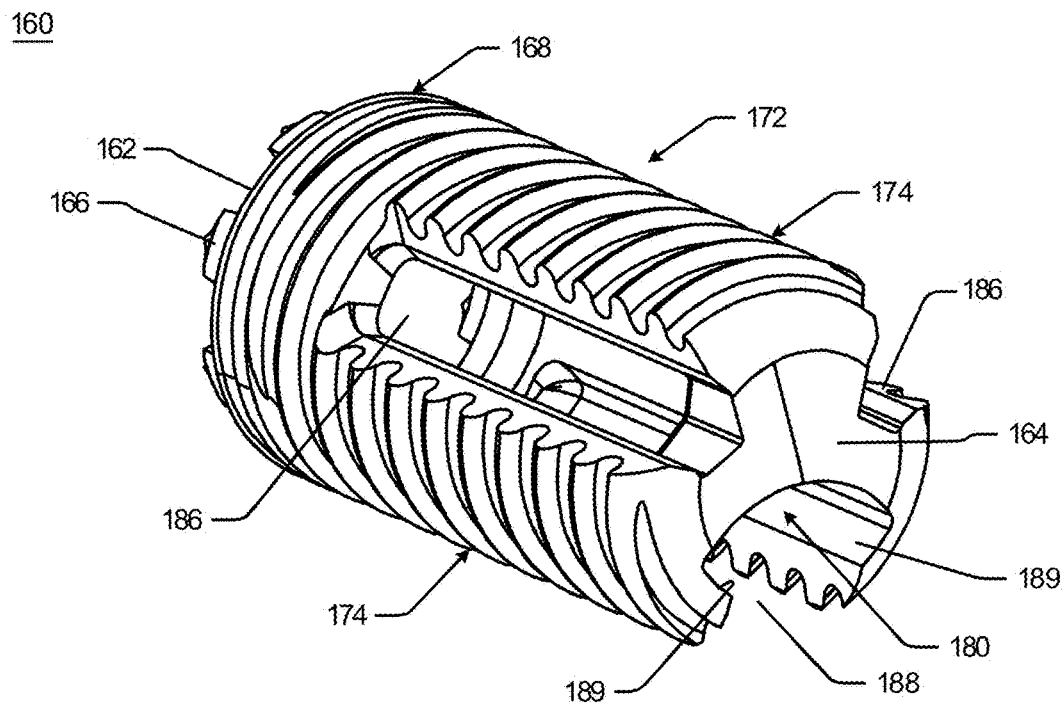
FIG. 25 is a first end perspective view of the extension member of FIG. 21, in accordance with an aspect of the present disclosure.

With continued reference to FIGS. 9-12 and reference to FIGS. 23-26, the extension member 160 is shown. The extension member 160 may include a first end 162 and second end 164. The first end 162 may include a plurality of protrusions, teeth, spikes, or engagement members 166, which may be, for example, positioned circumferentially around the first end 162. The protrusions 166 may be the same or similar to the engagement members 124 of the body 110. The protrusions 166 may have, for example, a polygonal shape with a generally rectangular cross-sectional shape and a pointed or triangularly shaped tip. The protrusions 166 may extend away from an attachment portion 168 of the extension member 160. The attachment portion 168 may include a groove 170 positioned, for example, circumferentially around the attachment portion 168 inferior to the engagement members 166. A translating portion 172 may extend away from the attachment portion 168 on a side opposite the engagement members 166. The translating portion 172 may be, for example, threaded from the attachment portion 168 to the second end 164 of the extension member 160. The translating portion 172 may include at least one leg member 174. As shown, the translating portion 172 includes, for example, three legs 174 spaced apart circumferentially around the extension member 160. The leg members 174 may be, for example, curved to enable the leg members 174 to engage an interior surface of and rotate with respect to the rotating member 140. The translating portion 172 and leg members 174 each include threads 176 around the exterior surface of the extension member 160. The threads 176 on the leg members 174 may be, for example, configured or sized and shaped to engage the threads 144 on the interior surface of the rotating member 140 to translate the extension member 160 with respect to the body 110. As shown in FIGS. 24 and 25, the extension member 160 may include a support member or stop pin seat 178 positioned at the second end 164 of the extension member 160. The support member 178 may couple to at least a portion of each of the three leg members 174.

Figure 26:
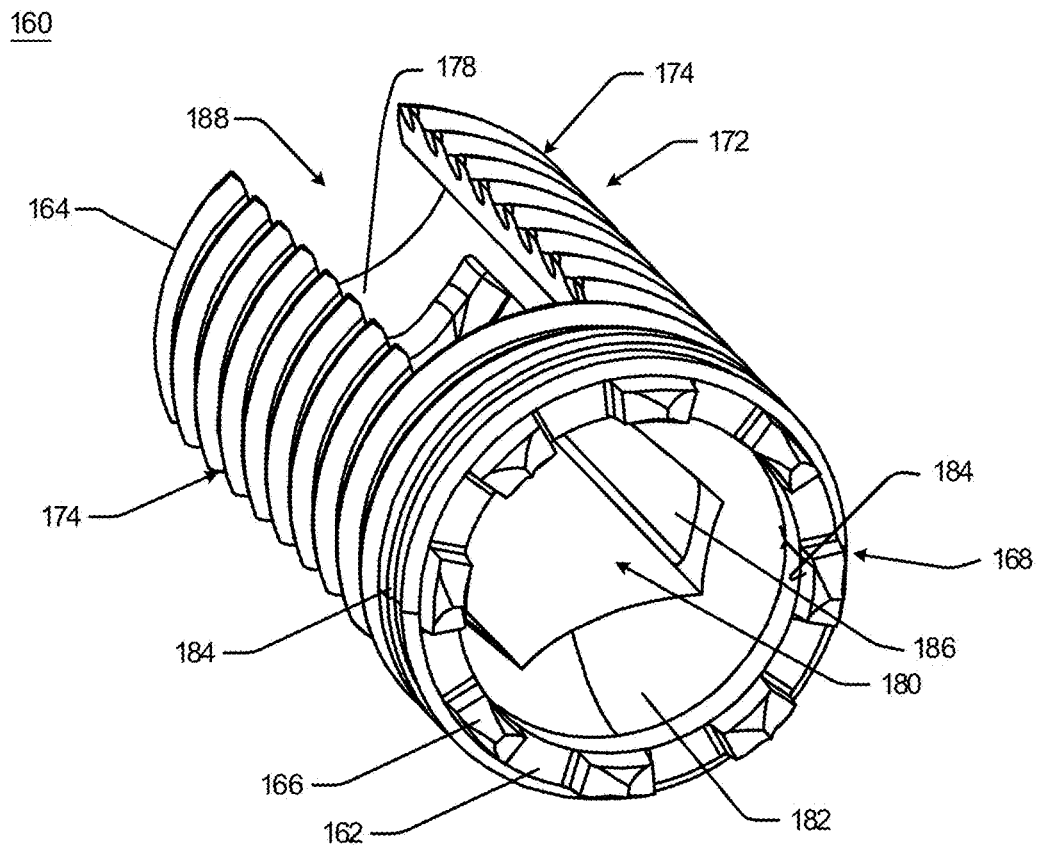
FIG. 26 is a second end perspective view of the extension member of FIG. 21, in accordance with an aspect of the present disclosure.
Figure 27:
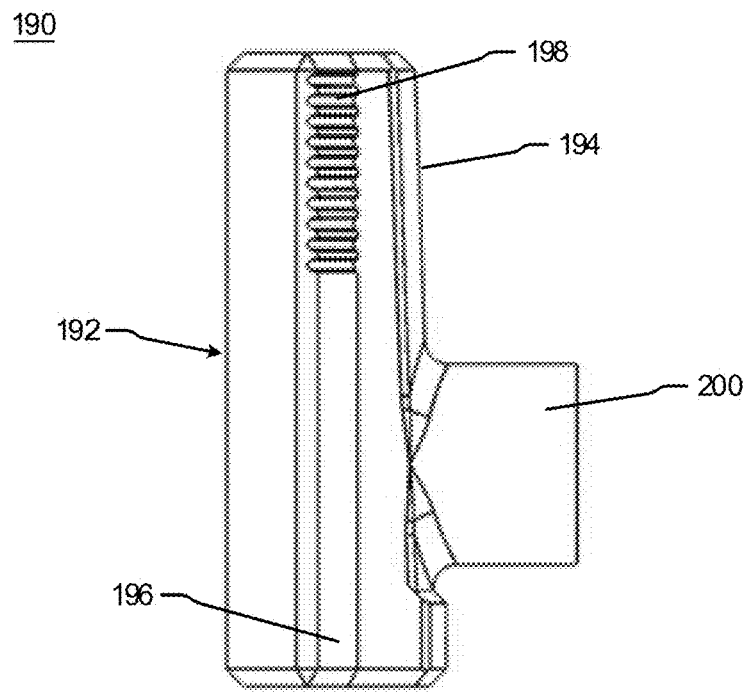
FIG. 27 is a side view of a locking member of the implant of FIG. 1, in accordance with an aspect of the present disclosure.
Figure 28:
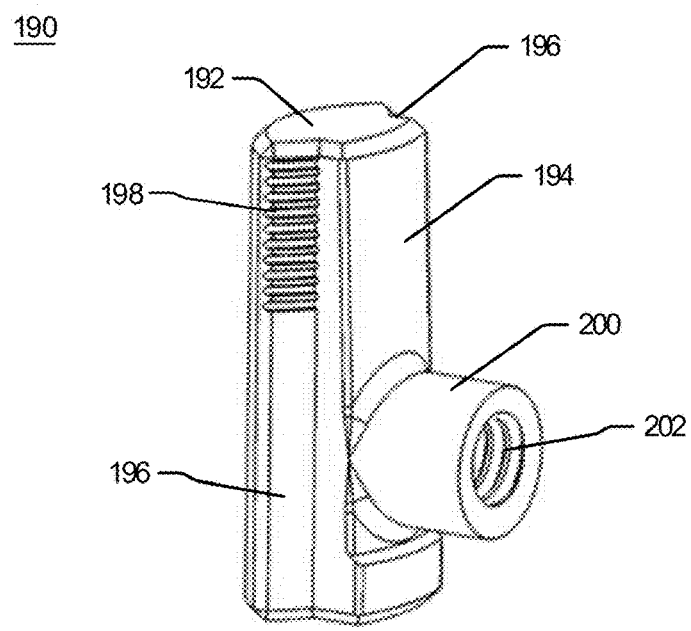
FIG. 28 is a perspective view of the locking member of FIG. 25, in accordance with an aspect of the present disclosure.

The extension member 160 may also include an opening 180, as shown in FIGS. 12 and 24-26. The opening 180 may, for example, extend through the center of the extension member 160 along a longitudinal axis of the extension member 160. The opening 180 forms an interior surface 182 on the interior of the extension member 160. As shown in FIGS. 24 and 26, the interior surface 182 near the first end 162 may be, for example, curved between the first end 162 and the leg members 174. The curved portion of the interior surface 182 may be, for example, a hemispherical or cylindrical shaped cup with the opening 180 passing through a center of the curved portion of the interior surface 182. The curved portion of the interior surface 182 and the center opening 180 may be, for example, configured or sized and shaped to receive autologous bone graft or allograft material which may be positioned to contact and allow for fusion with the adjacent vertebral bodies and additional graft material that may be positioned between the leg members 174. The curved portion of the interior surface 182 may also be, for example, configured or sized and shaped to allow the graft material to be positioned within the extension member 160 to minimize the height of the extension member 160 and entire implant 100. Further, the hemispherical shaped cup may be selected, for example, to minimize the amount of graft material necessary to fill the curved portion of the interior surface 182.

The extension member 160 may also include at least one alignment marking 184 positioned near the first end 162 of the extension member 160, as shown in FIG. 26. The at least one alignment marking 184 may include, for example, two alignment markings 184 positioned on an exterior of the extension member 160 and two alignment markings 184 positioned on the interior of the extension member 160 directly aligned with the two exterior alignment markings 184, as shown in FIG. 26. The first set of alignment markings 184 may be positioned directly across the opening 180 from the second set of alignment markings 184.

The extension member 160 may also include two through holes 186 extending through the extension member 160 from an exterior surface to an interior surface 182, as shown in FIG. 25. The two through holes 186 may include a first through hole 186 and a second through hole 186. The first through hole 186 may be positioned between a first and second leg member 174 and between the translation portion 172 adjacent to the attachment portion 168 and the support member 178. The second through hole 186 may be positioned between the second leg member 174 and a third leg member 174 and between the translation portion 172 adjacent to the attachment portion 168 and the support member 178. The extension member 160 may also include a channel 188 extending into the translation portion 172 from the second end 164 and to the translation portion 172 adjacent to the attachment portion 168. The channel 188 may be, for example, positioned between the first leg member 174 and the third leg member 174, as shown in FIG. 25. With continued reference to FIG. 25, the extension member 160 may also include recessed grooves 189 positioned on the interior surface 182 of the extension member 160 adjacent to the channel 188 for receiving the correspondingly shaped surfaces of the locking member 190, as described in greater detail below.

Referring now to FIGS. 9-12 and 27-28, the locking member or securement member 190 is shown. The locking member 190 includes a base portion 192 with a front surface 194 and a boss or engagement protrusion 200 coupled to and extending away from the front surface 194. The base portion 192 also includes engagement recesses or locking surfaces 196 extending into the front surface 194 at each side of the base portion 192. The size and shape of the engagement recesses 196 may correspond to or match the size and shape of the recessed grooves 189 of the extension member 160 to allow for the locking member 190 to slide within the channel 188 to allow for translation of the extension member 160 with respect to the body 110 once assembled. The locking member 190 may also include locking grooves 198 positioned along at least a portion of the engagement recesses 196 to assist with securing the implant 100 in the desired deployed position. The engagement protrusion 200 may have, for example, a cylindrical or round shape as it extends away from the front surface 194 of the base portion 192. The engagement protrusion 200 may also include a threaded opening 202 extending into the engagement protrusion 200 toward the base portion 192. The threaded opening 202 may be, for example, configured or sized and shaped to receiving an insertion instrument and/or a locking screw (not shown) to secure the extension member 160 to the body 110 in the desired position.

Figure 13:
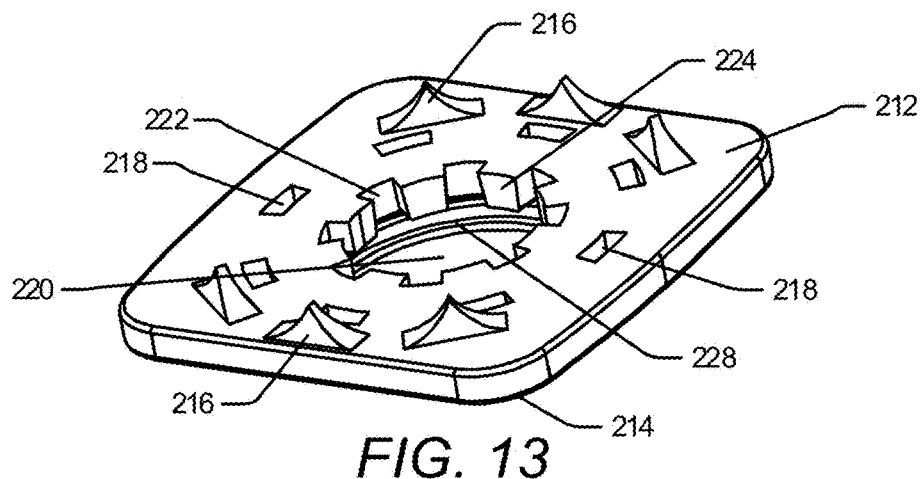
FIG. 13 is a first end, perspective view of a first end member of the implant of FIG. 1, in accordance with an aspect of the present disclosure.
Figure 14:
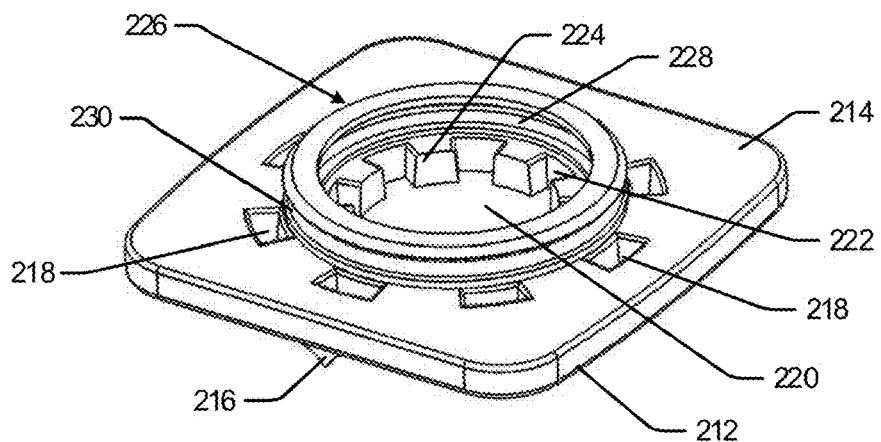
FIG. 14 is a second end, perspective view of the first end member of FIG. 13, in accordance with an aspect of the present disclosure.
Figure 15:
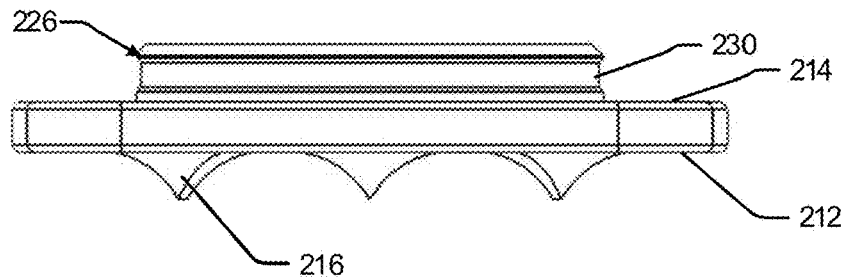
FIG. 15 is a side view of the first end member of FIG. 13, in accordance with an aspect of the present disclosure.

The end plate 210 may include a first end 212 and a second end 214, as shown in FIGS. 11-15. The end plate 210 may also include a coupling portion 226 extending away from the second end 214 of the end plate 210. The first end 212 of the end plate 210 may include a plurality of protrusions, spikes, or engagement members 216 extending away from the surface. The plurality of protrusions 216 may be, for example, generally triangularly shaped or pointed to engage a patient's bones. The end plate 210 may also include through holes or exterior alignment notches 218 extending through the end plate 210 from the first end 212 to the second end 214. The exterior alignment notches 218 may have, for example, a polygonal shape with a generally rectangular cross-sectional shape. The exterior alignment notches 218 may be positioned, for example, in a circle with a diameter larger than an exterior diameter of the coupling portion 226. The exterior alignment notches 218 may be, for example, positioned to receive the exterior engagement members 124 of the body 110, as described in greater detail below. The end plate 210 may also include an opening 220 extending through, for example, a center of the end plate 210 from the first end 212 to the second end 214. The opening 220 may include alternating interior alignment notches, grooves, or cutouts 222 and teeth or projections 224, as shown in FIGS. 13 and 14. The opening 220 form an interior surface extending through the end plate 210. The interior alignment notches 222 extend into the interior surface of the opening 220 and form the teeth or projections 224. The interior alignment notches 222 may have, for example, a polygonal shape. The interior alignment notches 222 may be, for example, positioned in a circle with a diameter smaller than the exterior diameter of the coupling portion 226. The interior alignment notches 222 may be, for example, positioned to receive the protrusions 166 of the first end 162 of the extension member 160, as described in greater detail below. The coupling protrusion 226 may include, for example, an interior slot 228 extending around the circumference of the interior surface of the coupling protrusion 226, as shown in FIGS. 13 and 14. The coupling protrusion 226 may also include, for example, an exterior slot 230 extending around the circumference of the exterior surface of the coupling protrusion 226, as shown in FIGS. 14 and 15. The exterior alignment notches 218 may be positioned, for example, circumferentially around the interior alignment notches 222 and the engagement members 216 may be positioned, for example, circumferentially around the exterior alignment notches 218. Thus, the diameter of the circle formed by the interior alignment notches 222 may be, for example, smaller than the diameter of the circles formed by both the exterior alignment notches 218 and the engagement members 216. In addition, the diameter of the circle formed by the engagement members 216 may be, for example, larger than the diameter of the circles formed by both the interior alignment notches 222 and the exterior alignment notches 218. It is also contemplated that the engagement members 216 may be positioned in alternative arrangements on the first end surface 212 of the end plate 210.

As shown in FIGS. 11 and 12, the end plate 240 may be as described above with reference to end plate 210, which will not be described again here for brevity sake.

Figure 16:
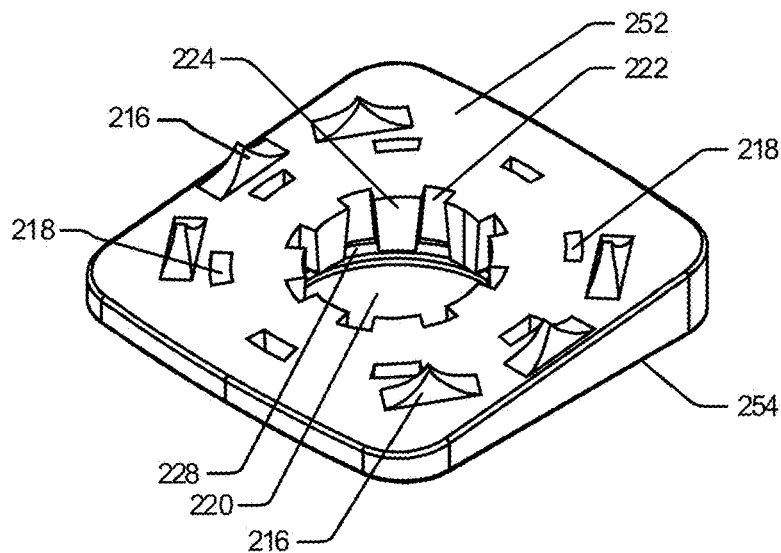
FIG. 16 is a first end perspective view of an alternative end member for the implant of FIG. 1, in accordance with an aspect of the present disclosure.
Figure 17:
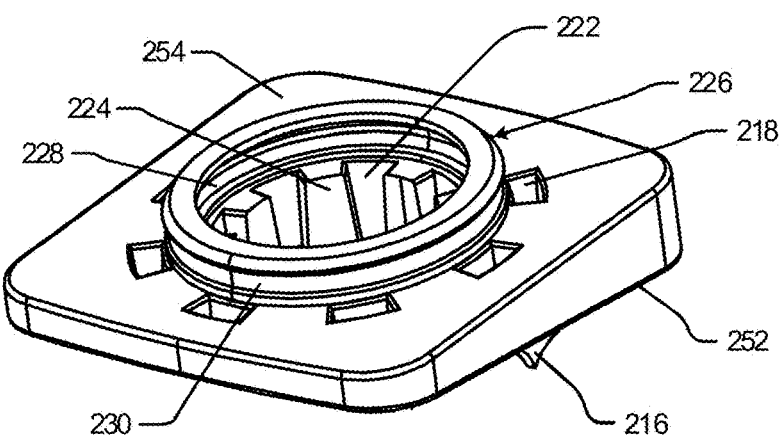
FIG. 17 is a second end perspective view of the alternative end member of FIG. 16, in accordance with an aspect of the present disclosure.
Figure 18:
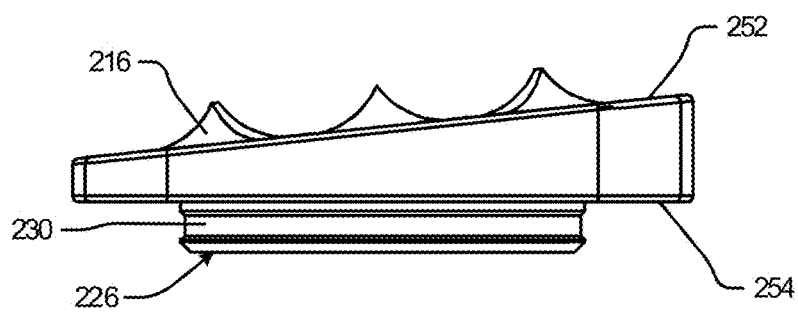
FIG. 18 is a side view of the alternative end member of FIG. 16, in accordance with an aspect of the present disclosure.
Figure 19:
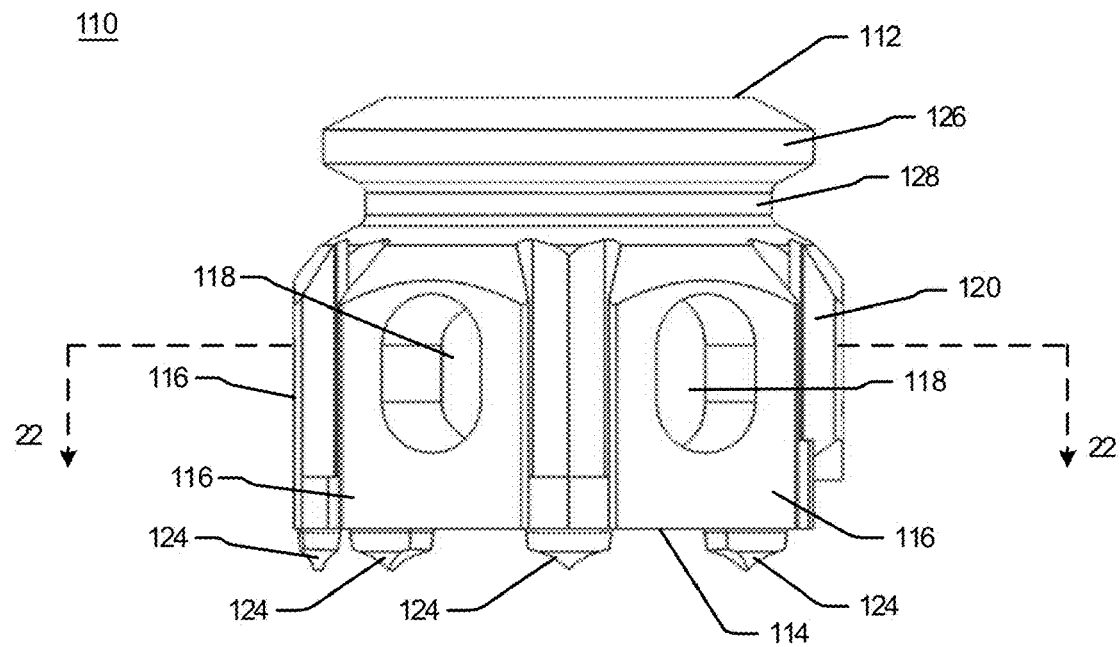
FIG. 19 is a side view of a body of the implant of FIG. 1, in accordance with an aspect of the present disclosure.

Referring now to FIGS. 16-18, another end plate 250 is shown. The end plate 250 may be an angled end plate 250 with the first end surface 252 being angled with respect to the second end surface 254. The angled first end surface 252 may provide, for example, an angled bone contacting surface. With the exception of the angled surfaces 252, 254, the end plate 250 is as described above with reference to end plate 210 and will not be described again here for brevity sake.

The vertebral body replacement device 100 may be assembled by obtaining a body 110 with a rotating member 140 rotatably coupled to the rim 126 and groove 128 of the first end 112 of the body 110. Next, the locking member 190 may be inserted into the through hole 130 of the body 110. The engagement protrusion 200 of the locking member 190 may be inserted into the opening 122 of the locking portion 120 from inside the body 110 to position the locking member 190 on an interior surface 132 of the body 110. Then, the extension member 160 may be inserted from, for example, a first end 112 of the body 110 to engage the exterior threads 176 of the extension member 160 with the interior threads 144 of the rotating member 140. The rotating member 140 may then be rotated to translate the leg members 174 of the extension member 160 into alignment with respect to the first alignment protrusion 134, the second alignment protrusion 136, and the locking member 190 on the interior surface 132 of the body 110. Once the leg members 174 are aligned with the channel 138 and the interior surface 132 on either side of the locking member 190, the rotating member 140 may be further rotated until the extension member 160 is translated into an undeployed or initial position. After the extension member 160 is positioned within the through hole 130 of the body 110, a pin 106 may be inserted through the locking hole 135 to retain the extension member 160 to the body 110. The pin 106 may also prevent the extension member 160 from being rotated out of engagement with the body 110.

Next, end plates 210, 240 may be coupled to the first and second ends of the implant 100. A first end plate 210 may be coupled to a first end 162 of the extension member 160. The first end plate 210 may be coupled by inserting a first O-ring 102 into the groove 170 of the extension member 160 and the interior slot 228 of the first end plate 210. In one embodiment, the first O-ring 102 may be inserted into the groove 170 of the extension member 160 and then the first end plate 210 may be pressed onto the extension member 160 to insert the first O-ring 102 into the interior slot 228 of the first end plate 210. Alternatively, the first O-ring 102 may be inserted into the interior slot 228 of the first end plate 210 and the first end plate 210 may be inserted onto the extension member 160 until the first O-ring 102 engages the groove 170 of the extension member 160. When coupling the first end plate 210 to the extension member 160, the protrusions 166 of the extension member 160 may be aligned with the interior alignment notches 222 of the first end plate 210. End plate 250 can be interchangeably coupled to the first end 162 of implant 100 in a manner similar to end plate 210, which will not be described again here for brevity sake.

The second end plate 240 may be coupled to a second end 114 of the body 110. The second end plate 240 may be coupled by inserting a second O-ring 104 into the interior slot 125 of the body 110 and the exterior slot 230 of the second end plate 240. In one embodiment, the second O-ring 104 may be inserted into the interior slot 125 of the body 110 and then the second end plate 240 may be pressed into the body 110 to insert the second O-ring 104 into the exterior slot 230 of the second end plate 240. Alternatively, the second O-ring 104 may be inserted into the exterior slot 230 of the second end plate 240 and the second end plate 240 may be inserted into the body 110 until the second O-ring 104 engages the interior slot 125 of the body 110. When coupling the second end plate 240 to the body 110, the engagement members 124 of the body 110 may be aligned with the exterior alignment notches 218 of the second end plate 240. Once assembled, a fastener (not shown) may optionally be partially screwed into place in the opening 202 of the engagement protrusion 200, so that the locking member 190 may be secured once the desired deployed position is achieved. End plate 250 can be interchangeably coupled to the second end 114 of implant 100 in a manner similar to end plate 240, which will not be described again here for brevity sake.

A method of using the vertebral body implant 100 may include obtaining a vertebral body implant 100 and an insertion instrument (not shown). The vertebral body implant 100 may be assembled as described in greater detail above, which will not be described again here for brevity's sake. The implant 100 may be, for example, coupled to an instrument (not shown) by the instrument engaging at least one side member 116 and/or locking protrusion 120. Once the implant 100 is coupled to the insertion instrument, the implant 100 may be inserted into the patient's spine in the desired location.

The insertion instrument may include at least one deployment handle (not shown) to engage the plurality of notches 146 of the rotating member 140. When the deployment handle is turned, the rotating member 140 turns and in turn translates the extension member 160 in a superior-inferior direction. As the rotating member 140 is rotated from an implanted or undeployed position, the extension member 160 will translate in a superior direction to expand the size of the implant 100. The amount of superior-inferior translation is limited by the length of the leg members 174. Once the extension member 160 is in a deployed position, the rotating member 140 may be rotated in either direction. If the deployment handle rotates the rotating member 140 in a reverse direction, the extension member 160 will translate in an inferior direction to decrease the height of the implant 100. When the desired height of the implant 100 is achieved, the locking member 190 may be tightened to lock or secure the extension member 160 with respect to the body 110. After the implant 100 is secured in the desired expanded position, the insertion tool (not shown) may be removed from the vertebral body implant 100.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants may include more or fewer components or features than the embodiments as described and illustrated herein. For example, the components and features of FIGS. 13-15 and FIGS. 16-18 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A vertebral body implant, comprising:
   a body with a first end and a second end, wherein the body further comprises:
      a through hole extending through the body from the first end to the second end forming an interior surface;
      a first alignment protrusion extending from the interior surface into the through hole; and
      a second alignment protrusion extending from the interior surface into the through hole;
      a circumferential protrusion positioned at the first end of the body;
      a groove inset into the body, and wherein the groove is positioned inferior to the circumferential protrusion;
      a plurality of side members extending from and positioned on an exterior surface of the body;
      an opening extending through each side member of the plurality of side members from the exterior surface to the interior surface;
      a plurality of engagement members extending away from the second end of the body;
      an interior slot extending into the interior surface toward the exterior surface, and wherein the interior slot is positioned near the second end of the body; and
      a locking hole positioned near the first end of the body, and wherein the locking hole extends through the first alignment protrusion to the exterior surface of the body;
   a rotating member rotatably coupled to the first end of the body;
   an extension member moveably coupled to the rotating member; and
   a locking member positioned on an interior of the body.

2. The vertebral body implant of claim 1, wherein the rotating member comprises:
   a plurality of first notches inset into one end of the rotating member;
   a center opening forming an interior surface, wherein the interior surface comprises:
      threads positioned on the interior surface;
   wherein the plurality of first notches open toward an inferior end; and
   a plurality of gear teeth positioned between the plurality of notches, wherein each gear tooth of the plurality of gear teeth includes a protrusion extending from an interior surface of each gear tooth toward the center opening.

3. The vertebral body implant of claim 2, wherein the protrusions of the plurality of gear teeth rotatably engage the groove of the body.

4. The vertebral body implant of claim 3, wherein the extension member comprises:
   an attachment portion positioned at a first end of the extension member; and
   a translating portion extending away from the attachment portion to a second end of the extension member.

5. The vertebral body implant of claim 4, wherein the attachment portion of the extension member comprises:
   a base portion;
   a groove extending into an exterior surface of the base portion of the extension member; and
   a plurality of protrusions extending away from the base portion at the first end of the extension member.

6. The vertebral body implant of claim 5, wherein the translating portion of the extension member comprises:
   a threaded portion extending away from the attachment portion;
   at least two leg members extending from the threaded portion to the second end of the extension member, wherein the at least two leg members comprise:
      threads positioned on an exterior surface of the at least two leg members and configured to engage the threads on the interior surface of the rotating member; and
      at least one through hole extending through the extension member adjacent to at least one of the at least two leg members, wherein the at least one through hole extends from an interior surface of the extension member to the exterior surface of the extension member; and
   a support member positioned between and coupled to the at least two leg members.

7. The vertebral body implant of claim 6, wherein the at least two leg members comprise:
   a first leg member;
   a second leg member; and
   a third leg member; and
   wherein the at least one through hole comprises:
      a first through hole positioned between the first leg member and the second leg member; and
      a second through hole positioned between the second leg member and the third leg member.

8. The vertebral body implant of claim 7, wherein the translating portion of the extension member further comprises:

a channel extending from the second end of the extension member to the threaded portion of the translating portion of the extension member;

wherein the channel is positioned between the first leg member and the third leg member; and wherein when the extension member is coupled to the body the locking member engages the channel, the first alignment protrusion engages the first through hole, and the second alignment protrusion engages the second through hole.

9. The vertebral body implant of claim 8, wherein the locking member comprises:
   a base portion, comprising:
      a front surface, a first side surface, and a second side surface;
      a first engagement recess inset into a first corner where the front surface engages the first side surface; and
      a second engagement recess inset into a second corner where the front surface engages the second side surface; and
   an engagement protrusion extending away from the front surface of the base portion, and wherein the engagement protrusion includes a threaded opening extending into the engagement protrusion toward the front surface of the base portion.

10. The vertebral body implant of claim 9, wherein the engagement protrusion of the locking member is received within the opening of a locking side member of the plurality of side members of the body.

11. The vertebral body implant of claim 10, wherein the base portion further comprises:
   at least one first locking groove positioned on the first engagement recess; and
   at least one second locking groove positioned on the second engagement recess.

12. The vertebral body implant of claim 9, wherein the vertebral body implant further comprises:
   at least one end plate coupled to at least one of the body and the extension member.

13. The vertebral body implant of claim 12, wherein the at least one end plate comprises:
   a plate portion; and
   a coupling protrusion extending away from a second end of the plate portion.

14. The vertebral body implant of claim 13, wherein the plate portion comprises:
   an opening extending from a first end of the plate portion through the coupling protrusion, wherein the opening forms an interior surface and the interior surface comprises:
      a plurality of interior alignment notches extending into the plate portion from the interior surface; and
      a plurality of projections, wherein a projection of the plurality of projections is positioned adjacent to each side of each interior alignment notch of the plurality of interior alignment notches;
   a plurality of exterior alignment notches extending through the plate portion from a first end to a second end, and wherein the plurality of exterior alignment notches are positioned between the opening and sides of the plate portion; and
   a plurality of engagement members extending away from the first end of the plate portion adjacent to the plurality of exterior alignment notches.

15. The vertebral body implant of claim 14, wherein the coupling protrusion comprises:

an interior slot extending from the opening into the coupling protrusion; and
an exterior slot extending from an exterior surface of the coupling protrusion toward the opening.

16. The vertebral body implant of claim 15, wherein the at least one end plate comprises:
   a first end plate coupled to the first end of the extension member; and
   a second end plate coupled to the second end of the body.

17. A method of assembling a vertebral body implant, comprising:
   obtaining a body with a rotating member rotatably coupled to the body, wherein the body further comprises:
      a through hole extending through the body from a first end to a second end forming an interior surface;
      a first alignment protrusion extending from the interior surface into the through hole; and
      a second alignment protrusion extending from the interior surface into the through hole;
      a circumferential protrusion positioned at the first end of the body;
      a groove inset into the body, and wherein the groove is positioned inferior to the circumferential protrusion;
      a plurality of side members extending from and positioned on an exterior surface of the body;
      an opening extending through each side member of the plurality of side members from the exterior surface to the interior surface;
      a plurality of engagement members extending away from the second end of the body;
      an interior slot extending into the interior surface toward the exterior surface, and wherein the interior slot is positioned near the second end of the body; and
      a locking hole positioned near the first end of the body, and wherein the locking hole extends through the first alignment protrusion to the exterior surface of the body;
   inserting a locking member into a through hole of the body;
   positioning the locking member on an interior surface of the body;
   inserting an extension member into a first end of the rotating member and a first end of the body;
   rotating the rotating member to translate the extension member to an undeployed position;
   coupling a first end plate to a first end of the extension member with a first retaining member; and
   coupling a second end plate to a second end of the body with a second retaining member.

18. A method of using a vertebral body implant, comprising:
   obtaining the vertebral body implant, the vertebral body implant comprising:
      a body with a first end and a second end, wherein the body further comprises:
         a through hole extending through the body from the first end to the second end forming an interior surface;
         a first alignment protrusion extending from the interior surface into the through hole; and
         a second alignment protrusion extending from the interior surface into the through hole;
         a circumferential protrusion positioned at the first end of the body;

a groove inset into the body, and wherein the groove is positioned inferior to the circumferential protrusion;

a plurality of side members extending from and positioned on an exterior surface of the body;

an opening extending through each side member of the plurality of side members from the exterior surface to the interior surface;

a plurality of engagement members extending away from the second end of the body;

an interior slot extending into the interior surface toward the exterior surface, and wherein the interior slot is positioned near the second end of the body; and a locking hole positioned near the first end of the body, and wherein the locking hole extends through the first alignment protrusion to the exterior surface of the body;

a rotating member rotatably coupled to the first end of the body;

an extension member moveably coupled to the rotating member; and a locking member positioned on an interior of the body;

obtaining an insertion instrument;

coupling the vertebral body implant to the insertion instrument;

inserting the vertebral body implant into a patient between two vertebral bodies;

engaging a plurality of first notches in the rotating member to translate the extension member in a first direction to expand the vertebral body implant; and removing the insertion instrument.

* * * * *